(12) United States Patent
Yukimura et al.

(10) Patent No.: US 8,183,403 B2
(45) Date of Patent: May 22, 2012

(54) ORGANOSILICON COMPOUND AS WELL AS RUBBER COMPOSITION, TIRE, PRIMER COMPOSITION, PAINT COMPOSITION AND ADHESIVE USING THE SAME

(75) Inventors: Noriaki Yukimura, Kodaira (JP); Yasuo Fukushima, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 12/918,771

(22) PCT Filed: Feb. 20, 2009

(86) PCT No.: PCT/JP2009/053090
§ 371 (c)(1),
(2), (4) Date: Nov. 16, 2010

(87) PCT Pub. No.: WO2009/104766
PCT Pub. Date: Aug. 27, 2009

(65) Prior Publication Data
US 2011/0054095 A1 Mar. 3, 2011

(30) Foreign Application Priority Data

Feb. 22, 2008 (JP) .................................. 2008-041973
May 21, 2008 (JP) .................................. 2008-133657

(51) Int. Cl.
*C07F 7/08* (2006.01)
(52) U.S. Cl. ........ 556/406; 556/407; 556/408; 556/413; 556/427
(58) Field of Classification Search .................. None
See application file for complete search history.

(56) References Cited

U.S. PATENT DOCUMENTS

| 3,468,751 | A |  | 9/1969 | Tesoro et al. |
|---|---|---|---|---|
| 3,842,111 | A |  | 10/1974 | Meyer-Simon et al. |
| 3,873,489 | A |  | 3/1975 | Thurn et al. |
| 3,997,581 | A | * | 12/1976 | Pletka et al. ................. 556/408 |
| 4,151,157 | A |  | 4/1979 | Williams et al. |
| 4,517,335 | A |  | 5/1985 | Wolff et al. |
| 2004/0181000 | A1 |  | 9/2004 | Araujo Da Silva et al. |
| 2005/0032949 | A1 |  | 2/2005 | Araujo Da Silva et al. |

FOREIGN PATENT DOCUMENTS

| JP | 48-37452 A | 6/1973 |
|---|---|---|
| JP | 59-232133 A | 12/1984 |
| JP | 2004-533522 A | 11/2004 |
| JP | 2005-536575 A | 12/2005 |
| JP | 2008-169157 A | 7/2008 |
| WO | WO 2007/085521 A1 | 8/2007 |
| WO | WO 2008/084885 A1 | 7/2008 |

OTHER PUBLICATIONS

Extended European Search Report dated Jan. 25, 2012 in corresponding European Patent Application No. EP 09712452.

* cited by examiner

*Primary Examiner* — Milton I Cano
*Assistant Examiner* — Wenwen Cai
(74) *Attorney, Agent, or Firm* — Sughrue Mion, PLLC

(57) ABSTRACT

This invention relates to a novel compound capable of largely reducing hysteresis loss of a rubber composition but also highly improving wear resistance, and more particularly to an organosilicon compound characterized by having one or more silicon-oxygen bond (Si—O) and 1-10 sulfur atoms (S) in its molecule, including one or more chain alkoxy groups and having one or more nitrogen atoms (N) at a position distant by 3-8 atoms from silicon atom (Si).

16 Claims, No Drawings

ORGANOSILICON COMPOUND AS WELL AS RUBBER COMPOSITION, TIRE, PRIMER COMPOSITION, PAINT COMPOSITION AND ADHESIVE USING THE SAME

CROSS REFERENCE TO RELATED APPLICATIONS

This application is a National Stage of International Application No. PCT/JP2009/053090 filed Feb. 20, 2009, claiming priority based on Japanese Patent Application No. 2008-041973 filed Feb. 22, 2008 and Japanese Patent Application No. 2008-133657 filed May 21, 2008, the contents of all of which are incorporated herein by reference in their entirety.

TECHNICAL FIELD

This invention relates to an organosilicon compound as well as a rubber composition, a primer composition, a paint composition and an adhesive each containing the organosilicon compound and a tire using the rubber composition, and more particularly to an organosilicon compound capable of reducing a hysteresis loss of a rubber composition and improving a wear resistance thereof.

RELATED ART

In recent years, it is demanded to improve safety of a tire on a wet road surface from a viewpoint of the safety of vehicles. Also, it is demanded to further lower fuel consumption of the vehicle from a viewpoint of the reduction of discharge amount of carbon dioxide associated with escalation in interest on environmental problem.

Heretofore, as a technique of establishing the improvement of tire performance on the wet road surface and the reduction of rolling resistance for these demands, there is known a method that it is effective to use an inorganic filler such as silica or the like as a filler of a rubber composition used in a tread of the tire. However, the rubber composition compounded with the inorganic filler such as silica or the like has a problem in the operability because the viscosity at the uncured state is high and multistage milling and the like are required though the rolling resistance of the tire is reduced and the braking property and steering stability on the wet road surface are improved. In the rubber composition compounded with the inorganic filler such as silica or the like, therefore, the break strength and wear resistance are largely deteriorated and problems such as vulcanization retardation, poor dispersion of the filler and the like are caused.

For this end, when the inorganic filler such as silica or the like is compounded into the rubber composition for the tread, the addition of a silane coupling agent is essential for lowering the viscosity at the uncured state of the rubber composition to ensure modulus and wear resistance and further lowering hysteresis loss (U.S. Pat. No. 3,842,111 and U.S. Pat. No. 3,873,489). Also, such a silane coupling agent is used in applications other than the rubber composition such as a primer composition, a paint composition, adhesive and so on.

DISCLOSURE OF THE INVENTION

However, since the silane coupling agent is expensive, the compounding cost may rise depending upon the compounding of the silane coupling agent. Also, the viscosity at the uncured state of the rubber composition is lowered even by the addition of a dispersion improver, whereby the operability is improved but the wear resistance is deteriorated. Further, when the dispersion improver is a high ionic compound, the deterioration of the processability such as adhesion to roll or the like is observed. In addition, the inventors have made investigations and found that even if the conventional silane coupling agent is added while compounding the inorganic filler such as silica or the like as a filler, the reduction of hysteresis loss and the improvement of wear resistance in the rubber composition can not be rendered into a fully satisfactory level and there is still a room for the improvement. Moreover, the silane coupling agent is also used in the primer composition, paint composition, adhesive and the like as mentioned above, but if an adherend is a hybrid material composed of an organic material and an inorganic material, the conventional silane coupling agent in the primer composition, paint composition, adhesive or the like is not sufficient in the adhesiveness or affinity at the interface between the organic material and the inorganic material, and hence it is found that there is still a room for improvement.

It is, therefore, an object of the invention to solve the problems of the conventional techniques and to provide a novel compound capable of largely reducing the hysteresis loss of the rubber composition and highly improving the wear resistance. Also, it is another object of the invention to provide a rubber composition, a primer composition, a paint composition and an adhesive each containing such a compound as well as a tire using such a rubber composition.

The inventors have made various studies in order to achieve the above objects and found that an organosilicon compound having one or more, preferably 1-6 silicon-oxygen bonds and 1-10 sulfur atoms in its molecule and one or more nitrogen atoms at a position distant by 3-8 atoms from silicon atom is high in the reaction rate to an inorganic filler such as silica or the like, so that when the organosilicon compound is compounded into a rubber component together with the inorganic filler, the efficiency of coupling reaction is increased to largely reduce the hysteresis loss of the rubber composition and highly improve the wear resistance but also the organosilicon compound has an effect of improving the adhesiveness or affinity at an interface between the organic material and the inorganic material in the hybrid material, and as a result, the invention has been accomplished.

That is, the organosilicon compound according to the invention is characterized by having one or more silicon-oxygen bond and 1-10 sulfur atoms in its molecule and including one or more chain alkoxy groups and having one or more nitrogen atoms at a position distant by 3-8 atoms from silicon atom.

In the organosilicon compound according to the invention, the number of silicon-oxygen bonds is preferable to be 1-6.

The organosilicon compound according to the invention is preferable to have a cyclic structure including nitrogen atom and silicon atom.

As the organosilicon compound according to the invention is preferable an organosilicon compound represented by the following general formula (I):

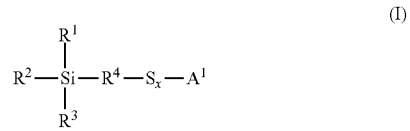

[wherein $A^1$ is represented by the following general formula (II) or (III):

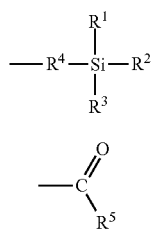

(II)

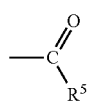

(III)

and at least one of $R^1$, $R^2$ and $R^3$ in the formulae (I) and (II) is represented by the following general formula (IV) or (V):

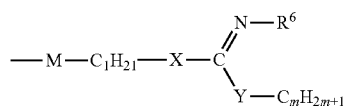

(IV)

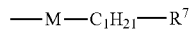

(V)

(wherein M is —O— or —CH$_2$—, and X and Y are independently —O—, —NR$^8$— or —CH$_2$—, and R$^6$ is —OR$^8$, —NR$^8$R$^9$ or —R$^8$, and R$^7$ is —NR$^8$R$^9$, —NR$^8$—NR$^8$R$^9$ or —N=NR$^8$ provided that R$^8$ is —C$_n$H$_{2n+1}$, R$^9$ is —C$_q$H$_{2q+1}$, and l, m, n and q are independently 0-10) and the other is -M-C$_l$H$_{2l+1}$ (wherein M and l have the same meanings as mentioned above), provided that M in one or more of $R^1$, $R^2$ and $R^3$ is —O—, and $R^4$ is represented by the following general formula (VI) or (VII):

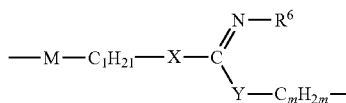

(VI)

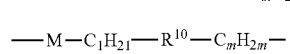

(VII)

(wherein M, X, Y, R$^6$, l and m have the same meanings as mentioned above, and R$^{10}$ is —NR$^8$—, —NR$^8$—NR$^8$— or —N=N— provided that R$^8$ has the same meaning as mentioned above) or by -M-C$_l$H$_{2l}$— (wherein M and l have the same meanings as mentioned above), and R$^5$ in the formula (III) is represented by the general formula (IV) or (V) or —C$_l$H$_{2l}$—R$^{11}$ (wherein R$^{11}$ is —NR$^8$R$^9$, —NR$^8$—NR$^8$R$^9$, —N=NR$^8$ or -M-C$_m$H$_{2m+1}$ provided that R$^8$, R$^9$, M, l and m have the same meanings as mentioned above), and x is 1-10].

Also, the organosilicon compound according to the invention is preferable to be an organosilicon compound represented by the following general formula (VIII):

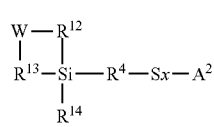

(VIII)

[wherein $A^2$ is represented by the following general formula (IX) or (III):

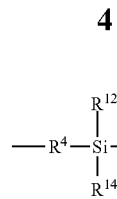

(IX)

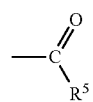

(III)

and W in the formulae (VIII) and (IX) is —NR$^8$—, —O— or —CR$^8$R$^{15}$— (wherein R$^{15}$ is —R$^9$ or —C$_m$H$_{2m}$—R$^7$, provided that R$^7$ is —NR$^8$R$^9$, —NR$^8$—NR$^8$R$^9$ or —N=NR$^8$, R$^8$ is —CH, R$^9$ is —C$_q$H$_{2q+1}$, and m, n and q are independently 0-10), R$^{12}$ and R$^{13}$ independently -M-C$_l$H$_{2l}$— (wherein M is —O— or —CH$_2$— and l is 0-10), R$^{14}$ is —O—C$_l$H$_{2l+1}$ or —O—C$_l$H$_{2l}$—R$^7$ (wherein R$^7$ and l have the same meanings as mentioned above), R$^4$ is represented by the following general formula (VI) or (VII):

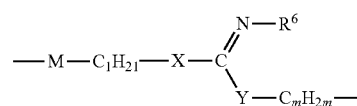

(VI)

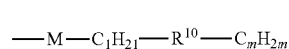

(VII)

(wherein M, l and m have the same meanings as mentioned above, and X and Y are independently —O—, —NR$^8$— or —CH$_2$—, and R$^6$ is —OR$^8$, —NR$^8$R$^9$ or —R$^8$, and R$^{10}$ is —NR$^8$—, —NR$^8$—NR$^8$— or —N=N— provided that R$^8$ and R$^9$ have the same meaning as mentioned above) or by -M-C$_l$H$_{2l}$— (wherein M and l have the same meaning as mentioned above), and R$^5$ in the formula (III) is represented by the following general formula (IV) or (V):

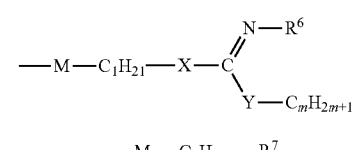

(IV)

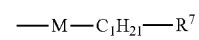

(V)

(wherein M, X, Y, R$^6$, R$^7$, l and m have the same meanings as mentioned above) or by —C$_l$H$_{2l}$—R$^{11}$ (wherein R$^{11}$ is —NR$^8$R$^9$, —NR$^8$—NR$^8$R$^9$, —N=NR$^8$ or -M-C$_m$H$_{2m+1}$ provided that R$^8$, R$^9$, M, l and m have the same meanings as mentioned above), x is 0-10].

In the preferable organosilicon compound, M is preferably —O—.

In the organosilicon compound of the formula (I), it is preferable that at least one of $R^1$, $R^2$ and $R^3$ is represented by —O—C$_l$H$_{2l}$—R$^7$ (wherein R$^7$ and l have the same meanings as mentioned above) and the other is represented by —O—C$_l$H$_{2l+1}$ (wherein l has the same meaning as mentioned above), R$^4$ is represented by —C$_l$H$_{2l}$— (wherein l has the same meaning as mentioned above), and $R^5$ is represented by —$C_lH_{2l}$—$R^{11}$ (wherein $R^{11}$ and l have the same meanings as mentioned above).

In the organosilicon compound of the formula (I), it is further preferable that at least one of $R^1$, $R^2$ and $R^3$ is represented by —O—$C_lH_{2l}$—$NR^8R^9$ (wherein $R^8$, $R^9$ and l have the same meanings as mentioned above), and $R^5$ is represented by —$C_lH_{2l+1}$ (wherein l has the same meaning as mentioned above).

In the organosilicon compound of the formula (VIII), it is preferable that W is represented by —$NR^8$— and $R^8$ is an alkyl group having a carbon number of 1-10.

In the organosilicon compound of the formula (VIII), it is also preferable that W is represented by —$NR^8$— (wherein $R^8$ has the same meaning as mentioned above), $R^{12}$ and $R^{13}$ are independently represented by —O—$C_lH_{2l}$— (wherein l has the same meaning as mentioned above), $R^{14}$ is represented by —O—$C_lH_{2l}$—$R^7$ (wherein $R^7$ and l have the same meanings as mentioned above), $R^4$ is represented by —$C_lH_{2l}$— (wherein l has the same meaning as mentioned above), and $R^5$ is represented by —$C_lH_{2l+1}$ (wherein l has the same meaning as mentioned above). At this moment, it is particularly preferable that W is represented by —$NR^8$—, and $R^8$ is an alkyl group having a carbon number of 1-10, and $A^2$ is represented by the general formula (III).

In the organosilicon compound of the formula (VIII), it is also preferable that W is represented by —O— or —$CR^8R^9$— (wherein $R^8$ and $R^9$ have the same meanings as mentioned above), $R^{12}$ and $R^{13}$ are independently represented by —O—$C_lH_{2l}$— (wherein l has the same meaning as mentioned above), $R^{14}$ is represented by —O—$C_lH_{2l}$—$NR^8R^9$ (wherein $R^8$, $R^9$ and l have the same meanings as mentioned above), $R^4$ is represented by —$C_lH_{2l}$— (wherein l has the same meaning as mentioned above), and $R^5$ is represented by —$C_lH_{2l+1}$ (wherein l has the same meaning as mentioned above).

Also, the rubber composition according to the invention is characterized by compounding an inorganic filler (B) and the above organosilicon compound (C) into a rubber component (A) comprising natural rubber and/or diene-based synthetic rubber.

In the rubber composition according to the invention, it is preferable that the inorganic filler (B) is compounded in an amount of 5-140 parts by mass per 100 parts by mass of the rubber component (A) comprising natural rubber and/or diene-based synthetic rubber and further the organosilicon compound (C) is included in an amount of 1-20 mass % of the amount of the inorganic filler (B) compounded.

In a preferable embodiment of the rubber composition according to the invention, the inorganic filler is silica or aluminum hydroxide. In this case, silica is preferable to have a BET surface area of 40-350 $m^2/g$.

Further, the tire according to the invention is characterized by using the above rubber composition.

In addition, the primer composition according to the invention is characterized by including the above organosilicon compound, and the paint composition according to the invention is characterized by including the above organosilicon compound, and the adhesive according to the invention is characterized by including the above organosilicon compound.

According to the invention, there can be provided an organosilicon compound containing nitrogen atom (N) and sulfur atom (S) and having a specified molecular structure with a chain alkoxy group and a silicon-oxygen bond (Si—O) and capable of largely reducing hysteresis loss of a rubber composition and highly improving wear resistance thereof. Also, there can be provided a rubber composition including the organosilicon compound, a tire using such a rubber composition, and further a primer composition, a paint composition and an adhesive each containing the organosilicon compound.

BEST MODE FOR CARRYING OUT THE INVENTION

<Organosilicon Compound>

The invention will be described in detail below. The organosilicon compound according to the invention is characterized by having one or more silicon-oxygen bonds (Si—O) and 1-10 sulfur atoms (S) in its molecule, including one or more chain alkoxy groups and having one or more nitrogen atoms (N) at a position distant by 3-8 atoms from silicon atom. Since the organosilicon compound include a nitrogen-containing functional group such as an amino group, an imino group, a substituted amino group, a substituted imino group or the like, which is high in the affinity with a surface of an inorganic filler such as silica or the like, at a position distant by 3-8 atoms from silicon atom (Si) in its molecular structure, an unshared electron pair of nitrogen atom is responsible for the reaction between the silane coupling agent and the inorganic filler such as silica or the like, and hence the rate of the coupling reaction is fast. Therefore, when the organosilicon compound of the formula (I) is added to the rubber composition compounded with the inorganic filler instead of the conventional silane coupling agent, the coupling efficiency is improved, and hence it is possible to highly improve the wear resistance while largely reducing the hysteresis loss of the rubber composition. Also, the organosilicon compound according to the invention contributes to the reduction of the compounding cost because the addition efficiency is high and the higher effect is obtained even in a small amount.

When the number of atoms between silicon atom (Si) and nitrogen atom (N) is less than 3 or exceeds 8, the coupling efficiency is not improved sufficiently, and hence the wear resistance can not be highly improved while largely reducing the hysteresis loss of the rubber composition. Moreover, the organosilicon compound according to the invention is preferable to have 1-6 silicon-oxygen bonds (Si—O). In this case, the reactivity with the inorganic filler such as silica or the like is high and the coupling efficiency is further improved.

The organosilicon compound according to the invention is preferable to have a cyclic structure including nitrogen atom (N) and silicon atom (Si). Even if the cyclic structure including nitrogen atom and sulfur atom includes silicon-oxygen bond (Si—O), such a cyclic structure is stable. Therefore, the formation of alcohol component is not caused by hydrolysis of silicon-oxygen bond, so that a gas of volatile organic compound (VOC) can be reduced in use. In the organosilicon compound having the cyclic structure, it is essential to have an alkoxy group of a chain structure for holding the reactivity with silica. If the cyclic structure including nitrogen atom and silicon atom does not include the chain alkoxy group in its ring, the reactivity with silica is largely deteriorated to lower the coupling efficiency.

More concretely, as the organosilicon compound of the invention are preferable compounds represented by the general formula (I) and compounds represented by the general formula (III). These organosilicon compounds may be used alone or in a combination of two or more.

<<Compounds of Formula (I)>>

In the general formula (I), $A^1$ is represented by the general formula (II) or (III), and x is 1-10. In this case, x is preferably a range of 2-4.

In the formulae (I) and (II), at least one of $R^1$, $R^2$ and $R^3$ is represented by the general formula (IV) or (V), and the other is represented by -M-$C_1H_{2l+1}$ (wherein M is —O— or —$CH_2$— and l is 0-10). In this regard, M in one or more of $R^1$, $R^2$ and $R^3$ is —O—. Since l is 0-10, —$C_1H_{2l+1}$ is hydrogen or an alkyl group having a carbon number of 1-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain.

In the formulae (IV) and (V), M is —O— or —$CH_2$—, and l is 0-10. In the formula (IV), m is 0-10.

In the formula (IV), X and Y are independently —O—, —$NR^8$— or —$CH_2$—. In this case, $R^8$ is —$C_nH_{2n+1}$ and n is 0-10. Since n is 0-10, —$C_nH_{2n+1}$ is hydrogen or an alkyl group having a carbon number of 1-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain.

In the formula (IV), $R^6$ is —$OR^8$, —$NR^8R^9$ or —$R^8$. In this case, $R^8$ is —$C_nH_{2n+1}$ and $R^9$ is —$C_qH_{2q+1}$, and n and q are independently 0-10. Moreover, —$C_nH_{2n+1}$ has the same meaning as mentioned above, and —$C_qH_{2q+1}$ is hydrogen or an alkyl group having a carbon number of 1-10 because q is 0-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain.

In the formula (V), $R^7$ is —$NR^8R^9$, —$NR^8$—$NR^8R^9$ or —N=$NR^8$. In this case, $R^8$ is —$C_nH_{2n+1}$ and $R^9$ is —$C_qH_{2q+1}$ and n and q are independently 0-10. Moreover, —$C_nH_{2n+1}$ and —$C_qH_{2q+1}$ have the same meanings as mentioned above.

In the formulae (I) and (II), $R^4$ is represented by the general formula (VI) or (VII) or -M-$C_1H_{2l}$—, and is particularly preferable to be represented by —$C_1H_{2l}$—. In this case, M is —O— or —$CH_2$— and l is 0-10. Since l is 0-10, —$C_1H_{2l}$— is a single bond or an alkylene group having a carbon number of 1-10. As the alkylene group having a carbon number of 1-10 are mentioned methylene group, ethylene group, trimethylene group, propylene group and so on. The alkylene group may be straight chain or branched chain.

In the formulae (VI) and (VII), M is —O— or —$CH_2$—, and l and m are 0-10. In the formula (VI), X and Y are independently —O—, —$NR^8$— or —$CH_2$—, and $R^6$ is —$OR^8$, —$NR^8R^9$ or —$R^8$. Moreover, $R^8$ and $R^9$ have the same meanings as mentioned above. In the formula (VII), $R^{10}$ is —$NR^8$—, —$NR^8$—$NR^8$— or —N=N—. In this case, $R^8$ is —$C_nH_{2n+1}$, and —$C_1H_{2l+1}$ has the same meaning as mentioned above.

Also, $R^5$ in the formula (III) is represented by the general formula (IV) or (V) or —$C_1H_{2l}$—$R^{11}$ and is particularly preferable to be represented by —$C_1H_{2l+1}$. In this case, $R^{11}$ is —$NR^8R^9$, —$NR^8$—$NR^8R^9$, —N=$NR^8$ or -M-$C_mH_{2m+1}$. However, $R^8$, $R^9$, M, l and m have the same meanings as mentioned above. Moreover, —$C_1H_{2l}$— and —$C_1H_{2l+1}$ have the same meanings as mentioned above. Since m is 0-10, —$C_mH_{2m+1}$ is hydrogen or an alkyl group having a carbon number of 1-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain.

In the compound of the formula (I), M is preferable to be —O— (oxygen). In this case, the reactivity with the inorganic filler such as silica or the like is high as compared with the compound wherein M is —CH2-.

Also, in the compound of the formula (I), it is preferable that at least one of $R^1$, $R^2$ and $R^3$ is represented by —O—$C_1H_{2l}$—$R^7$ and the other is represented by —O—$C_1H_{2l+1}$. $R^4$ is preferable to be represented by —$C_1H_{2l}$—, and $R^5$ is preferable to be represented by —$C_1H_{2l}$—$R^{11}$.

Further, in the compound of the formula (I), at least one of $R^1$, $R^2$ and $R^3$ is further preferable to be represented by —O—$C_1H_{2l}$—$NR^8R^9$, and $R^4$ is preferable to be represented by —$C_1H_{2l}$—, and $R^5$ is preferable to be represented by $C_1H_{2l+1}$.

<<Compounds of Formula (III)>>

In the general formula (III), $A^2$ is represented by the general formula (IX) or (III), and x is 1-10. In this case, X is preferably a range of 2-4.

In the formulae (VIII) and (IX), W is represented by —$NR^8$—, —O— or —$CR^8R^{15}$—, wherein $R^{15}$ is —$R^9$ or —$C_mH_{2m}$—$R^7$, provided that $R^7$ is —$NR^8R^9$, —$NR^8$—$NR^8R^9$ or —N=$NR^8$ and $R^8$ is —$C_nH_{2n+1}$ and $R^9$ is —$C_qH_{2q+1}$ and m, n and q are independently 0-10. Moreover, since m is 0-10, —$C_mH_{2m}$— is a single bond or an alkylene group having a carbon number of 1-10. As the alkylene group having a carbon number of 1-10 are mentioned methylene group, ethylene group, trimethylene group, propylene group and so on. The alkylene group may be straight chain or branched chain. Also, since n and q are 0-10, —$C_nH_{2n+1}$ and —$C_qH_{2q+1}$ are hydrogen or an alkyl group having a carbon number of 1-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain.

In the formulae (VIII) and (IX), $R^{12}$ and $R^{13}$ are independently represented by -M-$C_1H_{2l}$—, and $R^{14}$ is represented by —O—$C_1H_{2l+1}$ or —O—$C_1H_{2l}$—$R^7$, wherein M is —O— or —$CH_2$— and $R^7$ is —$NR^8R^9$, —$NR^8$—$NR^8R^9$ or —N=$NR^8$ and $R^8$ is —$C_nH_{2n+1}$ and $R^9$ is —$C_qH_{2q+1}$ and n and q are independently 0-10. Moreover, since l is 0-10, —$C_1H_{2l}$— is a single bond or an alkylene group having a carbon number of 1-10. As the alkylene group having a carbon number of 1-10 are mentioned methylene group, ethylene group, trimethylene group, propylene group and so on. The alkylene group may be straight chain or branched chain. Also, since l is 0-10, —$C_1H_{2l+1}$ is hydrogen or an alkyl group having a carbon number of 1-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain. Moreover, —$C_nH_{2n+1}$ and —$C_qH_{2q+1}$ have the same meanings as mentioned above.

In the formulae (VIII) and (IX), $R^4$ is represented by the general formula (VI) or (VII) or -M-$C_1H_{2l}$— and is particularly preferable to be represented by —$C_1H_{2l}$—. In this case, M is —O— or —$CH_2$— and l is 0-10. Moreover, —$C_1H_{2l}$— has the same meaning as mentioned above.

In the formulae (VI) and (VII), M is —O— or —$CH_2$—, and l and m are 0-10. In the formula (VI), X and Y are independently —O—, —$NR^8$— or —$CH_2$—, and $R^6$ is —$OR^8$, —$NR^8R^9$ or —$R^8$, wherein $R^8$ is —$C_nH_{2n+1}$ and $R^9$ is —$C_qH_{2q+1}$. In the formula (VII), $R^{10}$ is —$NR^8$—, —$NR^8$—

NR$^8$— or —N=N—, wherein R$^8$ is —C$_n$H$_{2n+1}$. Moreover, —C$_n$H$_{2n+1}$ and —C$_q$H$_{2q+1}$ have the same meanings as mentioned above.

Also, R$^5$ in the formula (III) is represented by the general formula (IV) or (V) or —C$_1$H$_{21}$—R$^{11}$ and is particularly preferable to be represented by —C$_1$H$_{21+1}$. In this case, R$^{11}$ is —NR$^8$R$^9$, NR$^8$—NR$^8$R$^9$, —N=NR$^8$ or -M-C$_m$H$_{2m+1}$, provided that R$^8$, R$^9$, M, l and m have the same meanings as mentioned above. Moreover, —C$_1$H$_{21}$— and —C$_1$H$_{21+1}$ have the same meanings as mentioned above. Since m is 0-10, —C$_m$H$_{2m+1}$ is hydrogen or an alkyl group having a carbon number of 1-10. As the alkyl group having a carbon number of 1-10 are mentioned methyl group, ethyl group, propyl group, butyl group, pentyl group, hexyl group, heptyl group, octyl group, decyl group and so on. The alkyl group may be straight chain or branched chain.

In the compound of the formula (VIII), M is preferable to be —O— (oxygen). In this case, the reactivity with the inorganic filler such as silica or the like is high as compared with the compound wherein M is —CH$_2$—.

When W is represented by —NR$^8$—, R$^8$ is preferable to be an alkyl group having a carbon number of 1-10. In this case, the cyclic structure is a tertiary amine structure. When the tertiary amine structure is compared with a secondary amine structure (R$^8$ is hydrogen), scorch time is very long and the burning of the uncured rubber can be prevented. Moreover, the alkyl group having a carbon number of 1-10 as R$^8$ has the same meaning as mentioned above.

Also, when W is represented by —NR$^8$—, R$^{12}$ and R$^{13}$ are preferable to be independently represented by —O—C$_1$H$_{21}$—, and R$^{14}$ is preferably represented by —O—C$_1$H$_{21}$—R$^7$, and R$^4$ is preferably represented by —C$_1$H$_{21}$—, and R$^5$ is preferably represented by —C$_1$H$_{21+1}$. Further, A$^2$ is particularly preferable to be represented by the formula (III).

On the other hand, when W is represented by —O— or —CR$^8$R$^9$—, R$^{12}$ and R$^{13}$ are preferable to be independently represented by —O—C$_1$H$_{21}$—, and R$^{14}$ is preferably represented by —O—C$_1$H$_{21}$—NR$^8$R$^9$, and R$^4$ is preferably represented by —C$_1$H$_{21}$—, and R$^5$ is preferably represented by —C$_1$H$_{21+1}$.

<<Method of Synthesizing Organosilicon Compound>>

The organosilicon compound according to the invention can be synthesized by adding an amine compound such as 2-(dimethylamino)ethanol, 2-(diethylamino)ethanol, 2-(dimethylamino)propanol, 2-(diethylamino)propanol, N-methyldiethanol amine or the like to a compound of the general formula (I) wherein R$^1$, R$^2$ and R$^3$ are represented by -M-C$_1$H$_{21+1}$ and M in one or more of R$^1$, R$^2$ and R$^3$ is —O— and further adding an acid such as p-toluene sulfonic acid, hydrochloric acid or the like or a titanium alkoxide such as titanium tetra-n-butoxide or the like as a catalyst and then heating to substitute one or more of R$^1$, R$^2$ and R$^3$ with a monovalent nitrogen-containing group represented by the formula (IV) or (V) or substitute R$^1$ and R$^2$ with a bivalent nitrogen-containing group represented by —R$^{12}$—W—R$^{13}$—.

<<Concrete Example of Organosilicon Compound>>

As the organosilicon compound according to the invention are concretely mentioned 3-octanoylthiopropyl(mono-dimethylaminoethoxy) diethoxysilane, 3-octanoylthiopropyl(didimethylaminoethoxy) monoethoxysilane, 3-octanoylthiopropyl tri-dimethylamino ethoxysilane, 3-octanoylthiopropyl(mono-diethylaminoethoxy) diethoxysilane, 3-octanoylthiopropyl(mono-dimethylaminopropyloxy) diethoxysilane, 3-octanoylthiopropyl(mono-diethylaminopropyloxy) diethoxysilane, 3-octanoylthiopropyl (ethoxy) 1,3-dioxa-5-methylaza-2-silacyclohexane, 3-octanoylthiopropyl(ethoxy) 1,3-dioxa-5-ethylaza-2-silacyclohexane, 3-octanoylthiopropyl(ethoxy) 1,3-dioxa-6-methylaza-2-silacyclohexane, 3-octanoylthiopropyl(ethoxy) 1,3-dioxa-6-ethylaza-2-silacyclohexane, bis(3-(mono-dimethylaminoethoxy)diethoxysilyl-propyl) disulfide, bis(3-(di-dimethylaminoethoxy)monoethoxysilyl-propyl) disulfide, bis(3-(tri-dimethylaminoethoxy)silyl-propyl) disulfide, bis (3-(mono-dimethylaminoethoxy)diethoxysilyl-propyl) disulfide, bis(3-(mono-diethylaminoethoxy)diethoxysilyl-propyl) disulfide, bis(3-(mono-dimethylaminopropyloxy) diethoxysilyl-propyl) disulfide, bis(3-(mono-diethylaminopropyloxy)diethoxysilyl-propyl) disulfide, bis (3-(mono-dimethylaminoethoxy)diethoxysilyl-propyl) tetrasulfide, bis(3-(di-dimethylaminoethoxy)monoethoxysilyl-propyl) tetrasulfide, bis(3-(tri-dimethylaminoethoxy)silyl-propyl) tetrasulfide, bis(3-(mono-dimethylaminoethoxy) diethoxysilyl-propyl) tetrasulfide, bis(3-(mono-diethylaminoethoxy)diethoxysilyl-propyl) tetrasulfide, bis (3-(mono-dimethylaminopropyloxy)diethoxysilyl-propyl) tetrasulfide, bis(3-(mono-diethylaminopropyloxy)diethoxysilyl-propyl) tetrasulfide, bis(3-(ethoxy) 1,3-dioza-5-methylaza-2-silacyclohexyl-propyl) disulfide, bis(3-(ethoxy) 1,3-dioxa-5-ethylaza-2-silacyclohexyl-propyl) disulfide, bis (3-(ethoxy) 1,3-dioxa-6-methylaza-2-silacyclohexyl-propyl) disulfide, bis(3-(ethoxy) 1,3-dioxa-6-ethylaza-2-silacyclohexyl-propyl) disulfide, bis(3-(ethoxy) 1,3-dioxa-5-methylaza-2-silacyclohexyl-propyl) tetrasulfide, bis(3-(ethoxy) 1,3-dioxa-5-ethylaza-2-silacyclohexyl-propyl) tetrasulfide, bis(3-(ethoxy) 1,3-dioxa-6-methylaza-2-silacyclohexyl-propyl) tetrasulfide, and bis(3-(ethoxy) 1,3-dioxa-6-ethylaza-2-silacyclohexyl-propyl) tetrasulfide.

<Rubber Composition>

The rubber composition according to the invention is characterized by compounding the inorganic filler (B) and the organosilicon compound (C) into the rubber component (A) composed of natural rubber and/or diene-based synthetic rubber. Preferably, 5-104 parts by mass of the inorganic filler (B) is compounded based on 100 parts by mass of the rubber component (A) composed of natural rubber and/or diene-based synthetic rubber, and further the organosilicon compound (C) is compounded in an amount of 1-20 mass % of the amount of the inorganic filler (B) compounded.

In this case, when the amount of the organosilicon compound is less than 1 mass % of the amount of the inorganic filler (B) compounded, the effect of reducing the hysteresis loss of the rubber composition and the effect of improving the wear resistance are insufficient, while when it exceeds 20 mass %, the effects are saturated.

The rubber component (A) in the rubber composition according to the invention is natural rubber and/or diene-based synthetic rubber. As the diene-based synthetic rubber are mentioned styrene-butadiene copolymer rubber (SBR), polybutadiene rubber (BR), polyisoprene rubber (IR), butyl rubber (IIR), ethylene-propylene copolymer and so on. These rubber components (A) may be used alone or in a blend of two or more.

As the inorganic filler (B) used in the rubber composition of the invention are mentioned silica, aluminum hydroxide, alumina, clay, calcium carbonate and the like. Among them, silica and aluminum hydroxide are preferable from a viewpoint of the reinforcing property, and silica is particularly preferable. When the inorganic filler (B) is silica, since the organosilicon compound (C) has a functional group having a high affinity with a silanol group on the surface of silica and/or a functional group having a high affinity with silicon atom (Si), the coupling efficiency is highly improved to reduce the hysteresis loss of the rubber composition, and the effect of improving the wear resistance becomes more remarkable. Moreover, silica is not particularly limited, so that wet-process silica (silicic hydrate), dry-process silica (silicic anhydride) and the like may be used. On the other hand, as the aluminum hydroxide is preferably used HIGI-LITE (registered trade mark, made by SHOWA DENKO Co., Ltd.).

The silica is preferable to have a BET surface area of 40-350 m$^2$/g. When the BET surface area of silica is less than 40 m$^2$/g, the particle size of silica is too large and the wear resistance is largely deteriorated, while when the BET surface area of silica exceeds 350 m$^2$/g, the particle size of silica is too small and the hysteresis loss is largely increased.

The amount of the inorganic filler (B) compounded is a range of 5-140 parts by mass per 100 parts by mass of the rubber component (A). When the amount of the inorganic filler (B) compounded is less than 5 parts by mass per 100 parts by mass of the rubber component (A), the effect of reducing the hysteresis loss is insufficient, while when it exceeds 140 parts by mass, the operability is considerably deteriorated.

In addition to the rubber component (A), inorganic filler (B) and organosilicon compound (C), the rubber composition according to the invention may be properly compounded with additives usually used in the rubber industry such as carbon black, softening agent, vulcanizing agent, vulcanization accelerator, antioxidant, zinc white, stearic acid and so on for any purpose. As these additives may be preferably used commercially available ones. Moreover, the rubber composition according to the invention may be produced by compounding the rubber component (A) with the inorganic filler (B) and organosilicon compound (C) and, if necessary, various additives properly selected and then milling, warming and extruding them.

<Tire>

The tire according to the invention is characterized by using the above rubber composition, wherein it is preferable to use the rubber composition in a tread. In the tire according to the invention, the rolling resistance is largely reduced but also the wear resistance is highly improved. Moreover, the tire according to the invention has the conventionally known structure and is not particularly limited, and can be manufactured by the usual method. When the tire of the invention is a pneumatic tire, as a gas to be filled in the tire may be used an inert gas such as nitrogen, argon, helium or the like in addition to usual air or air having a regulated oxygen partial pressure.

<Primer Composition, Paint Composition and Adhesive>

Furthermore, the primer composition of the invention is characterized by including the organosilicon compound, and the paint composition of the invention is characterized by including the organosilicon compound, and the adhesive of the invention is characterized by including the organosilicon compound. Since the organosilicon compound according to the invention has a high affinity even with a hydroxy group other than silanol group, the reaction with the various inorganic compounds having hydroxy group can be promoted, and hence there is an effect in the improvement of adhesiveness at the interface of the hybrid material composed of organic material and inorganic material and the improvement of the affinity. Therefore, the primer composition, paint composition and adhesive each including the organosilicon compound can improve the adhesiveness and affinity in the interface between the organic material and inorganic material.

At this moment, the primer composition of the invention may contain a catalyst comprised of a metal such as tin, titanium or the like or a metal compound as a cure-promoting component in addition to the organosilicon compound, or may contain an organic solvent for adjusting the viscosity of the primer composition. Also, the paint composition of the invention may contain a pigment, metal particles, a resin and further an organic solvent or water in addition to the organosilicon compound. Furthermore, the adhesive of the invention may contain a resin and further an organic solvent for adjusting the viscosity of the adhesive in addition to the organosilicon compound. Moreover, each of the primer composition, paint composition and adhesive according to the invention can be prepared according to a well-known method by mixing the organosilicon compound with additives properly selected for any purpose and a solvent.

EXAMPLES the following examples are given in illustration of the invention and are not intended as limitations thereof.

Production Example 1 of Organosilicon Compound

Into a Kjeldahl flask of 200 mL are charged 40 g of bis(3-(triethoxysilylpropyl) disulfide [a compound represented by the formula (I) wherein A$^1$ is the formula (II) and R$^1$ is —O—CH$_2$CH$_3$ and R$^2$ is —O—CH$_2$CH$_3$ and R$^3$ is —O—CH$_2$CH$_3$ and R$^4$ is —CH$_2$CH$_2$CH$_2$— and x is 2], 7.5 g of 2-(dimethylamino) ethanol and 0.5 g of p-toluene sulfonic acid at room temperature. The resulting red solution is heated at 145-150° C. until the occurrence of bubbles is stopped. Then, 7.5 g of 2-(dimethylamino) ethanol is added dropwise through a dropping funnel over 30 minutes, and thereafter ethanol is removed at 85° C. and 45 mmHg with a rotary evaporator to obtain an organosilicon compound (C-1). As analyzed by $^1$H-NMR, the resulting organosilicon compound (C-1) is confirmed to be a compound having 0.7 (t; 2H), 1.2 (t; 9H), 1.8 (m; 2H), 2.3 (s; 6H), 2.5 (t; 2H), 2.7 (t; 2H) and 3.8 (m; 6H) and represented by the formula (I) wherein A$^1$ is the formula (II) and R$^1$ is —O—CH$_2$CH$_3$ and R$^2$ is —O—CH$_2$CH$_3$ and R$^3$ is —O—CH$_2$CH$_2$N(CH$_3$)$_2$ [i.e. represented by the formula (V) wherein M is —O— and l is 2 and R$^7$ is —N(CH$_3$)$_2$] and R$^4$ is —CH$_2$CH$_2$CH$_2$— and x is 2.

Production Example 2 of Organosilicon Compound

Into a Kjeldahl flask of 200 mL are charged 40 g of 3-octanoylthiopropyl triethoxysilane [a compound represented by the formula (I) wherein A$^1$ is the formula (III) and R$^1$ is —O—CH$_2$CH$_3$ and R$^2$ is —O—CH$_2$CH$_3$ and R$^3$ is —O—CH$_2$CH$_3$ and R$^4$ is —CH$_2$CH$_2$CH$_2$— and R$^5$ is —C$_7$H$_{is}$ and x is 1], 4.9 g of 2-(dimethylamino) ethanol and 0.5 g of p-toluene sulfonic acid at room temperature. The resulting red solution is heated at 145-150° C. until the occurrence of bubbles is stopped. Then, 4.9 g of 2-(dimethylamino) ethanol is added dropwise through a dropping funnel over 30 minutes, and thereafter ethanol is removed at 85° C. and 45 mmHg with a rotary evaporator to obtain an organosilicon compound (C-2). As analyzed by $^1$H-NMR, the resulting organosilicon compound (C-2) is confirmed to be a compound having 0.7 (t; 2H), 0.9 (t; 3H), 1.2 (t; 6H), 1.4 (m; 8H), 1.7 (m; 4H), 2.3 (s; 6H), 2.5 (m; 4H), 2.9 (t; 2H) and 3.8 (m; 6H) and represented by the formula (I) wherein A$^1$ is the formula (III) and R$^1$ is —O—CH$_2$CH$_3$ and R$^2$ is —O—CH$_2$CH$_3$ and R$^3$ is —O—CH$_2$CH$_2$N(CH$_3$)$_2$ [i.e. represented by the formula (V) wherein M is —O— and l is 2 and R$^7$ is —N(CH$_3$)$_2$] and R$^4$ is —CH$_2$CH$_2$CH$_2$— and R$^5$ is —C$_7$H$_{is}$ and x is 1.

Production Example 3 of Organosilicon Compound

Into a four-necked Kjeldahl flask of 500 mL are weighed 60 g of 3-octanoylthiopropyl triethoxysilane [compound represented by the formula (I) wherein $A^1$ is the formula (III) and $R^1$ is —O—$CH_2CH_3$ and $R^2$ is —O—$CH_2CH_3$ and $R^3$ is —O—$CH_2CH_3$ and $R^4$ is —$CH_2CH_2CH_2$— and $R^5$ is $C_7H_{15}$, and x is 1], 20 g of N-methyldiethanol amine, 0.8 g of titanium tetra-n-butoxide and 220 mL of toluene. Then, the flask is heated in an oil bath while stirring with a mechanical stirrer and flowing a dry nitrogen (0.2 L/min) and then a Dimroth condenser is attached thereto to conduct reflux for 11 hours. Thereafter, the solvent is removed at 20 hPa/40° C. with a rotary evaporator and subsequently the remaining volatile matter is removed with a rotary pump (10 Pa) and a cold trap (dry ice+ethanol) to obtain 70 g of a yellowish transparent liquid. As analyzed by $^1$H-NMR, the resulting organosilicon compound (C-3) is confirmed to be a compound having 0.7 (t; 2H), 0.9 (t; 3H), 1.2 (t; 3H), 1.4 (m; 8H), 1.7 (m; 4H), 2.4 (s; 3H), 2.5 (m; 6H), 2.9 (t; 2H) and 3.8 (m; 6H) and represented by the formula (VIII) wherein $A^2$ is the formula (III) and W is —N($CH_3$)— and $R^{12}$ is —O—$CH_2CH_2$— (provided that a side of O is connected to Si) and $R^{13}$ is —O—$CH_2CH_2$— (provided that a side of O is connected to Si) and $R^{14}$ is —O—$CH_2CH_3$ and $R^4$ is —$CH_2CH_2CH_2$— and $R^5$ is —$C_7H_{15}$ and x is 1.

Production Example 4 of Organosilicon Compound

Into a four-necked Kjeldahl flask of 500 mL are weighed 40 g of bis(3-triethoxysilylpropyl) disulfide [compound represented by the formula (I) wherein $A^1$ is the formula (II) and $R^1$ is —O—$CH_2CH_3$ and $R^2$ is —O—$CH_2CH_3$ and $R^3$ is —O—$CH_2CH_3$ and $R^4$ is —$CH_2CH_2CH_2$— and x is 2], 20 g of N-methyldiethanol amine, 0.8 g of titanium tetra-n-butoxide and 220 mL of toluene. Then, the flask is heated in an oil bath while stirring with a mechanical stirrer and flowing a dry nitrogen (0.2 L/min) and then a Dimroth condenser is attached thereto to conduct reflux for 11 hours. Thereafter, the solvent is removed at 20 hPa/40° C. with a rotary evaporator and subsequently the remaining volatile matter is removed with a rotary pump (10 Pa) and a cold trap (dry ice+ethanol) to obtain 50 g of a yellowish transparent liquid. As analyzed by $^1$H-NMR, the resulting organosilicon compound (C-4) is confirmed to be a compound having 0.7-0.83 ppm (m; 4H), 1.17-1.27 ppm (m; 6H), 1.77-1.91 ppm (m; 4H), 2.34-2.45 ppm (s; 6H), 2.50-3.05 ppm (m; 12H) and 3.70-3.85 ppm (m; 12H) and represented by the formula (VIII) wherein $A^2$ is the formula (IX) and W is —N($CH_3$)— and $R^{12}$ is —O—$CH_2CH_2$— (provided that a side of O is connected to Si) and $R^{13}$ is —O—$CH_2CH_2$-(provided that a side of O is connected to Si) and $R^{14}$ is —O—$CH_2CH_3$ and $R^4$ is —$CH_2CH_2CH_2$— and x is 2.

<Preparation and Evaluation of Rubber Composition>

A rubber composition is prepared by milling a compounding recipe shown in Tables 1-4 with a Banbury mixer. Then, properties of a vulcanizate obtained from the resulting rubber composition are measured by the following methods. The results are shown in Tables 1-4.

(1) Dynamic Viscoelasticity

Tan δ of the vulcanized rubber is measured using a spectrometer made by Ueshima Seisakusho Co., Ltd. (machine for measuring dynamic viscoelasticity) under conditions that a frequency is 52 Hz, an initial strain is 10%, a measuring temperature is 60° C. and a dynamic strain is 1%, and represented by an index on the basis that the value of tan δ of Comparative Example 1 is 100 in Table 1, the value of tan δ of Comparative Example 3 is 100 in Table 2, the value of tan δ of Comparative Example 5 is 100 in Table 3, and the value of tan δ of Comparative Example 7 is 100 in Table 4. The smaller the index value, the lower the tan δ and the lower the heat buildup of the rubber composition.

(2) Test for Wear Resistance

The test is conducted according to JIS K6264-2:2005 with a Lambourn abrasion tester at room temperature and a slip ratio of 25%, and the wear resistance is represented by an index on the basis that a reciprocal of a worn amount in Comparative Example 1 is 100 in Table 1, a reciprocal of a worn amount in Comparative Example 3 is 100 in Table 2, a reciprocal of a worn amount in Comparative Example 5 is 100 in Table 3 and a reciprocal of a worn amount in Comparative Example 7 is 100 in Table 4. The larger the index value, the smaller the worn amount and the better the wear resistance.

TABLE 1

| | | | Comparative Example 1 | Comparative Example 2 | Example 1 | Example 2 |
|---|---|---|---|---|---|---|
| Compounding recipe | Emulsion polymerized SBR-1 *1 | parts by mass | 100 | 100 | 100 | 100 |
| | Carbon black-1 N220 *2 | | 10 | 10 | 10 | 10 |
| | Silica *3 | | 50 | 50 | 50 | 50 |
| | Silane compound-1 *4 | | 4 | 5 | — | — |
| | Organosilicon compound (C-1) | | — | — | 4.7 | 5.9 |
| | Aromatic oil | | 30 | 30 | 30 | 30 |
| | Stearic acid | | 2.0 | 2.0 | 2.0 | 2.0 |
| | Antioxidant 6PPD *5 | | 1.0 | 1.0 | 1.0 | 1.0 |
| | Antioxidant TMDQ *6 | | 1.0 | 1.0 | 1.0 | 1.0 |
| | Zinc oxide | | 2.5 | 2.5 | 2.5 | 2.5 |
| | Vulcanization accelerator DPG *7 | | 0.6 | 0.6 | 0.6 | 0.6 |
| | Vulcanization accelerator MBTS *8 | | 1.0 | 1.0 | 1.0 | 1.0 |
| | Vulcanization | | 0.6 | 0.6 | 0.6 | 0.6 |

TABLE 1-continued

|  |  |  | Comparative Example 1 | Comparative Example 2 | Example 1 | Example 2 |
|---|---|---|---|---|---|---|
|  | accelerator TBBS *9 |  |  |  |  |  |
|  | Sulfur |  | 1.5 | 1.5 | 1.5 | 1.5 |
| Properties of | Tan δ | index | 100 | 99 | 86 | 84 |
| vulcanizate | Wear resistance | index | 100 | 103 | 104 | 106 |

*1 Emulsion polymerized SBR #1500, made by JSR Corporation
*2 #80, made by Asahi Carbon Co., Ltd.
*3 Nipsil AQ, made by Nippon Silica Kogyo Co., Ltd. BET surface area = 220 $m^2$/g
*4 bis(3-triethpxysilylpropyl) disulfide
*5 Nocrac 6C, made by OUCHI SHINKO Chemical Industrial Co., Ltd.
*6 Nocrac 224, made by OUCHI SHINKO Chemical Industrial Co., Ltd.
*7 Sanseler D, made by SANSHIN Chemical Industry Co., Ltd.
*8 Sanseler DM, made by SANSHIN Chemical Industry Co., Ltd.
*9 Sanseler NS, made by SANSHIN Chemical Industry Co., Ltd

TABLE 2

|  |  |  | Comparative Example 3 | Comparative Example 4 | Example 3 | Example 4 |
|---|---|---|---|---|---|---|
| Compounding recipe | Emulsion polymerized SBR-2 *10 | parts by mass | 137.5 | 137.5 | 137.5 | 137.5 |
|  | Carbon black-1 N220 *2 |  | 15 | 15 | 15 | 15 |
|  | Silica *3 |  | 65 | 65 | 65 | 65 |
|  | Silane compound-2 *11 |  | 5.2 | 6.5 | — | — |
|  | Organosilicon compound (C-2) |  | — | — | 5.8 | 7.3 |
|  | Stearic acid |  | 2.0 | 2.0 | 2.0 | 2.0 |
|  | Antioxidant 6PPD *5 |  | 1.0 | 1.0 | 1.0 | 1.0 |
|  | Antioxidant TMDQ *6 |  | 1.0 | 1.0 | 1.0 | 1.0 |
|  | Zinc oxide |  | 2.5 | 2.5 | 2.5 | 2.5 |
|  | Vulcanization accelerator DPG *7 |  | 1.0 | 1.0 | 1.0 | 1.0 |
|  | Vulcanization accelerator MBTS *8 |  | 1.0 | 1.0 | 1.0 | 1.0 |
|  | Vulcanization accelerator TBBS *9 |  | 1.0 | 1.0 | 1.0 | 1.0 |
|  | Sulfur |  | 1.5 | 1.5 | 1.5 | 1.5 |
| Properties of | Tan δ | index | 100 | 98 | 99 | 98 |
| vulcanizate | Wear resistance | index | 100 | 102 | 116 | 118 |

*2, *3, *5, *6, *7, *8 and *9 are the same as in Table 1
*10 Emulsion polymerized SBR #1712, made by JSR Corporation, oil-extended with 37.5 parts by mass of aromatic oil per 100 parts by mass of rubber component
*11 3-octanoylthio-propyl triethoxysilane

TABLE 3

|  |  |  | Comparative Example 5 | Comparative Example 6 | Example 5 |
|---|---|---|---|---|---|
| Compounding recipe | Emulsion polymerized SBR-3 *12 | parts by mass | 100.0 | 100.0 | 100.0 |
|  | Carbon black-2 N220 *13 |  | 10.0 | 10.0 | 10.0 |
|  | Silica *3 |  | 50.0 | 50.0 | 50.0 |
|  | Organosilicon compound (C-3) |  | — | — | 7.0 |
|  | Silane Compound-1 *4 |  | 7.0 | — | — |
|  | Silane compound-2 *11 |  | — | 7.0 | — |
|  | Aromatic oil |  | 30.0 | 30.0 | 30.0 |
|  | Stearic acid |  | 2.0 | 2.0 | 2.0 |
|  | Antioxidant |  | 1.5 | 1.5 | 1.5 |

TABLE 3-continued

|  |  |  | Comparative Example 5 | Comparative Example 6 | Example 5 |
|---|---|---|---|---|---|
|  | 6PPD *5 |  |  |  |  |
|  | Zinc oxide |  | 2.5 | 2.5 | 2.5 |
|  | Vulcanization accelerator DPG *7 |  | 1.0 | 1.0 | 1.0 |
|  | Vulcanization accelerator MBTS *8 |  | 1.0 | 1.0 | 1.0 |
|  | Vulcanization accelerator CBS *14 |  | 1.0 | 1.0 | 1.0 |
|  | Sulfur |  | 1.5 | 1.5 | 1.5 |
| Properties of vulcanizate | Tan δ | index | 100 | 82 | 91 |
|  | Wear resistance | index | 100 | 98 | 102 |

*3, *4, *5, *7, *8 and *11 are the same as in Tables 1 and 2.
*12 Emulsion polymerized SBR 1500, made by JSR Corporation
*13 #78, made by Asahi Carbon Co., Ltd.
*14 N-cyclohexylbenzothiazole-2-sulfenamide

TABLE 4

|  |  |  | Comparative Example 7 | Comparative Example 8 | Comparative Example 9 | Example 6 | Example 7 |
|---|---|---|---|---|---|---|---|
| Compounding recipe | Emulsion polymerized SBR-4 *15 | parts by mass | 100 | 100 | 100 | 100 | 100 |
|  | Carbon black-2 N220 *13 |  | 10 | 10 | 10 | 10 | 10 |
|  | Silica *3 |  | 50 | 50 | 50 | 50 | 50 |
|  | Silane compound-1 *4 |  | 5.0 | — | — | — | — |
|  | Silane compound-2 *11 |  | — | 5.0 | — | — | — |
|  | Silane compound-3 *16 |  | — | — | 5.0 | — | — |
|  | Organosilicon compound (C-3) |  | — | — | — | 5.0 | — |
|  | Organosilicon compound (C-4) |  | — | — | — | — | 5.0 |
|  | Aromatic oil |  | 30 | 30 | 30 | 30 | 30 |
|  | Stearic acid |  | 2.0 | 2.0 | 2.0 | 2.0 | 2.0 |
|  | Antioxidant 6PPD *5 |  | 1.0 | 1.0 | 1.0 | 1.0 | 1.0 |
|  | Antioxidant TMDQ *6 |  | 1.0 | 1.0 | 1.0 | 1.0 | 1.0 |
|  | Zinc oxide |  | 2.5 | 2.5 | 2.5 | 2.5 | 2.5 |
|  | Vulcanization accelerator DPG*7 |  | 0.6 | 0.6 | 0.6 | 0.6 | 0.6 |
|  | Vulcanization accelerator MBTS *8 |  | 1.0 | 1.0 | 1.0 | 1.0 | 1.0 |
|  | Vulcanization accelerator TBBS *9 |  | 0.6 | 0.6 | 0.6 | 0.6 | 0.6 |
|  | Sulfur |  | 1.5 | 1.5 | 1.5 | 1.5 | 1.5 |
| Properties of vulcanizate | Tan δ | index | 100 | 82 | 84 | 81 | 90 |
|  | Wear resistance | index | 100 | 85 | 74 | 101 | 108 |

*3, *4, *5, *6, *7, *8, *9, *11 and *13 are the same as in Tables 1, 2 and 3.
*15 Emulsion polymerized SBR #0122, made by JSR Corporation
*16 3-octanoylthiopropyl silatrane As seen from Tables 1 to 4, the wear resistance can be improved highly while largely reducing the tan δ and hence hysteresis loss of the rubber composition to lower the heat buildup by compounding the organosilicon compound (C) according to the invention instead of the conventional silane coupling agent (*4, *11 and *16).

The invention claimed is:

1. An organosilicon compound characterized by having one or more silicon-oxygen bond and 1-10 sulfur atoms in its molecule, including one or more chain alkoxy groups and having one or more nitrogen atoms at a position distant by 3-8 atoms from silicon atom, which is represented by the following general formula (VIII):

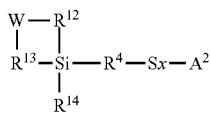

(VIII)

[wherein $A^2$ is represented by the following general formula (IX) or (III):

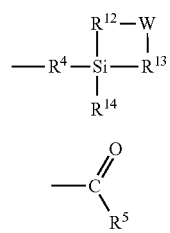

(IX)

(III)

and W in the formulae (VIII) and (IX) is $-NR^8-$, $-O-$ or $-CR^8R^{15}-$ (wherein $R^{15}$ is $-R^9$ or $-C_mH_{2m}-R^7$, provided that $R^7$ is $-NR^8R^9$, $-NR^8-NR^8R^9$ or $-N=NR^8$, $R^8$ is $-CH$, $R^9$ is $-C_qH_{2q+1}$, and m, n and q are independently 0-10), $R^{12}$ and $R^{13}$ are independently $-M-C_lH_{2l}-$ (wherein M is $-O-$ or $-CH_2-$ and l is 0-10), $R^{14}$ is $-O-C_lH_{2l+1}$ or $-O-C_lH_{2l}-R^7$ (wherein $R^7$ and l have the same meanings as mentioned above), $R^4$ is represented by the following general formula (VI) or (VII):

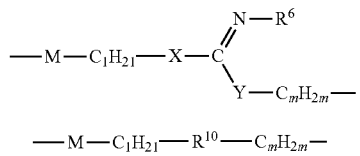

(VI)

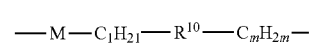

(VII)

(wherein M, l and m have the same meanings as mentioned above, and X and Y are independently $-O-$, $-NR^8-$ or $-CH_2-$, and $R^6$ is $-OR^8$, $-NR^8R^9$ or $-R^8$, and $R^{10}$ is $-NR^8-$, $-NR^8-NR^8-$ or $-N=N-$ provided that $R^8$ and $R^9$ have the same meaning as mentioned above) or by $-M-C_lH_{2l}-$ (wherein M and l have the same meaning as mentioned above), and $R^5$ in the formula (III) is represented by the following general formula (IV) or (V):

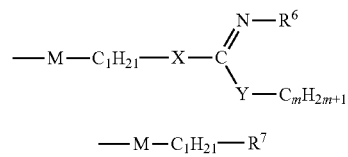

(IV)

(V)

(wherein M, X, Y, $R^6$, $R^7$, l and m have the same meanings as mentioned above) or by $-C_lH_{2l}-R^{11}$ (wherein $R^{11}$ is $-NR^8R^9$, $-NR^8-NR^8R^9$, $-N=NR^8$ or $-M-C_mH_{2m+1}$ provided that $R^8$, $R^9$, M, l and m have the same meanings as mentioned above), x is 1-10].

2. An organosilicon compound according to claim 1, wherein the number of silicon-oxygen bonds is 1-6.

3. An organosilicon compound according to claim 1, which has a cyclic structure including nitrogen atom and silicon atom.

4. An organosilicon compound according to claim 1, wherein M is $-O-$.

5. An organosilicon compound according to claim 1, wherein W is represented by $-NR^8-$ and $R^8$ is an alkyl group having a carbon number of 1-10.

6. An organosilicon compound according to claim 1, wherein W is represented by $-NR^8-$ (wherein $R^8$ has the same meaning as mentioned above), $R^{12}$ and $R^{13}$ are independently represented by $-O-C_lH_{2l}-$ (wherein l has the same meaning as mentioned above), $R^{14}$ is represented by $-O-C_lH_{2l}-R^7$ (wherein $R^7$ and l have the same meanings as mentioned above), $R^4$ is represented by $-C_lH_{2l}-$ (wherein l has the same meaning as mentioned above), and $R^5$ is represented by $-C_lH_{2l+1}$ (wherein l has the same meaning as mentioned above).

7. An organosilicon compound according to claim 5, wherein W is represented by $-NR^8-$, and $R^8$ is an alkyl group having a carbon number of 1-10, and $A^2$ is represented by the general formula (III).

8. An organosilicon compound according to claim 1, wherein W is represented by $-O-$ or $-CR^8R^9-$ (wherein $R^8$ and $R^9$ have the same meanings as mentioned above), $R^{12}$ and $R^{13}$ are independently represented by $-O-C_lH_{2l}-$ (wherein l has the same meaning as mentioned above), $R^{14}$ is represented by $-O-C_lH_{2l}-NR^8R^9$ (wherein $R^8$, $R^9$ and l have the same meanings as mentioned above), $R^4$ is represented by $-C_lH_{2l}-$ (wherein l has the same meaning as mentioned above), and $R^5$ is represented by $-C_lH_{2l+1}$ (wherein l has the same meaning as mentioned above).

9. A primer composition characterized by including an organosilicon compound as claimed in claim 1.

10. A paint composition characterized by including an organosilicon compound as claimed in claim 1.

11. An adhesive characterized by including an organosilicon compound as claimed in claim 1.

12. A rubber composition characterized by compounding an inorganic filler (B) and an organosilicon compound (C) as claimed in claim 1 into a rubber component (A) comprising natural rubber and/or diene-based synthetic rubber.

13. A rubber composition according to claim 12, wherein the inorganic filler (B) is compounded in an amount of 5-140 parts by mass per 100 parts by mass of the rubber component (A) comprising natural rubber and/or diene-based synthetic rubber and further the organosilicon compound (C) is included in an amount of 1-20 mass% of the amount of the inorganic filler (B) compounded.

14. A rubber composition according to claim 12, wherein the inorganic filler is silica or aluminum hydroxide.

15. A rubber composition according to claim 14, wherein silica has a BET surface area of 40-350 m²/g.

16. A tire characterized by using a rubber composition as claimed in claim 12.

* * * * *